United States Patent [19]

Van Tassel et al.

[11] Patent Number: 4,531,943
[45] Date of Patent: Jul. 30, 1985

[54] CATHETER WITH SOFT DEFORMABLE TIP

[75] Inventors: Robert A. Van Tassel, Minnetonka; Mark A. Rydell, Excelsior; Gilmore T. Schjeldahl, Minnetonka, all of Minn.

[73] Assignee: Angiomedics Corporation, Minneapolis, Minn.

[21] Appl. No.: 520,996

[22] Filed: Aug. 8, 1983

[51] Int. Cl.$^3$ ............................................ A61M 25/00
[52] U.S. Cl. ..................................... 604/280; 604/96; 128/658
[58] Field of Search ......................... 604/280, 96, 281; 128/206.14, 658, 248.1

[56] References Cited

U.S. PATENT DOCUMENTS

| | | |
|---|---|---|
| 3,605,750 | 9/1971 | Sheridan et al. .................... 128/658 |
| 3,635,223 | 1/1972 | Klieman . |
| 3,865,666 | 2/1975 | Shoney . |
| 4,003,369 | 1/1977 | Heilman et al. . |
| 4,207,900 | 6/1980 | Patel et al. . |
| 4,239,042 | 12/1980 | Asai . |
| 4,280,500 | 7/1981 | Ono . |
| 4,350,169 | 9/1982 | Dutcher et al. . |
| 4,385,635 | 5/1983 | Ruiz . |
| 4,419,095 | 12/1983 | Nebergall et al. .................... 604/96 |

Primary Examiner—Stephen C. Pellegrino
Attorney, Agent, or Firm—Orrin M. Haugen; Thomas J. Nikolai; Douglas L. Tschida

[57] ABSTRACT

A catheter for insertion in a body orifice or blood vessel comprising an elongated tubular body with a soft, symmetrically deformable member on the distal end thereof for decreasing the likelihood of injury to body tissue upon the insertion and removal thereof. In one embodiment, the tip member comprises a toroidally shaped inflatable and non-distensible expandable "balloon" mounted on the end of the otherwise relatively rigid tip of the catheter. The catheter has a lumen extending the length thereof and communicating with the tip member whereby a fluid may be introduced to control the size, shape and firmness of the tip member. In a second embodiment, the soft deformable tip member comprises an annular plastic or rubber sleeve surrounding the otherwise rigid tip of the catheter and normally extending there beyond by a predetermined distance. The thickness or composition of the sleeve is varied about a circumferential ring so as to provide a preferred location for the collapse of the sleeve.

13 Claims, 6 Drawing Figures

U.S. Patent  Jul. 30, 1985  4,531,943
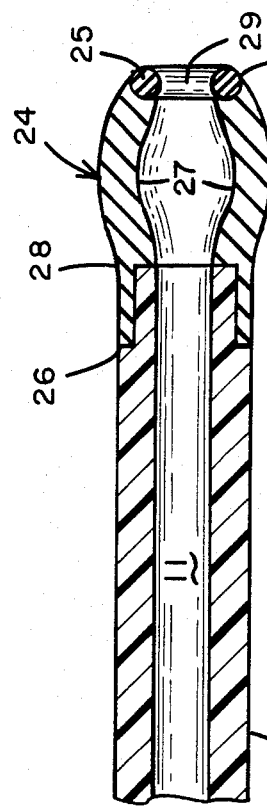
Fig. 4
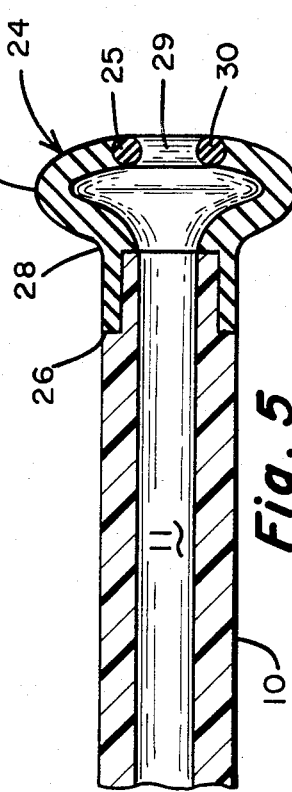
Fig. 5
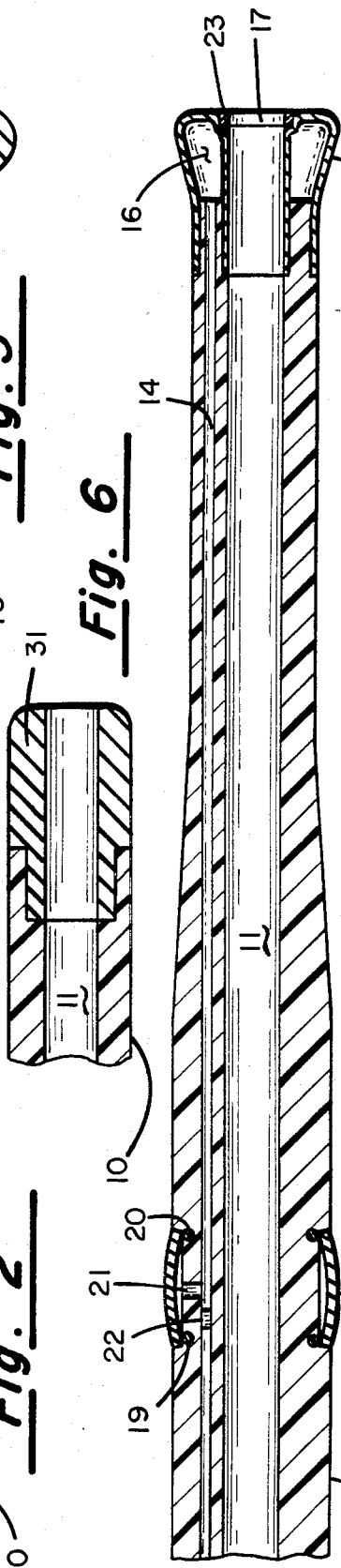
Fig. 3
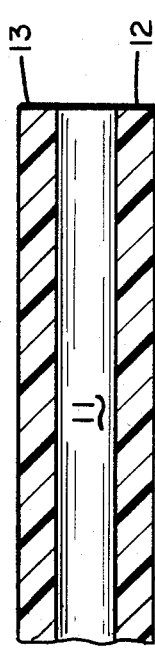
PRIOR ART
Fig. 1
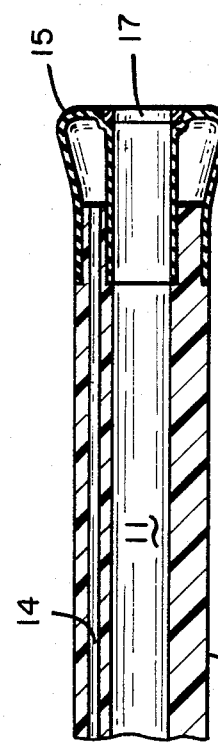
Fig. 2
Fig. 6

CATHETER WITH SOFT DEFORMABLE TIP

BACKGROUND OF INVENTION

I. Field of the Invention

This invention relates generally catheter structures adapted to be introduced into a living body, and more specifically to the design of a catheter which may be introduced and routed through the vascular system of a patient with a minimum of damage or trauma to endothelial tissue.

II. Discussion of the Prior Art

Present day surgical procedures permit the introduction of tubular catheters into the vascular system of a body. For example, angiographic catheters are commonly introduced into the femoral artery and routed through the arterial system and to the coronary ostium so that radiopaque contrast or medicaments may be injected as part of a diagnostic or treatment procedure. Typically, such catheters comprise elongated, flexible plastic tubes of a predetermined small diameter significantly less than the cross section of the vessels through which the catheter must pass. Other forms of catheters which the present invention may find use are those associated with cardiac pacemakers. Here, the catheter takes the form of a pacing lead which is typically made to pass through the subclavian vein and through the superior vena cava into the right ventrical of the heart. Here, the catheter takes the form of a flexible sheath surrounding elongated conductors which terminate at the distal end in one or more surface electrodes adapted to contact endocardial heart tissue.

Prior art, angiographic and other diagnostic catheters as well as cardiac pacing leads are generally formed from polyethylene, polyurethane, polypropylene or silicone rubber or other non-thrombogenic material. So that they may be passed through the vascular system without folding or buckling, they must possess a wall thickness and a hardness which is capable of damaging vascular tissue, especially where the distal tip of the catheter is blunt or possessed of a sharp edge. While perhaps rare, there have been instances where small diameter catheters having sharp edged tips have been advanced through the wall of the aorta, resulting in the death of the patient.

SUMMARY OF THE INVENTION

The present invention obviates the above-described problems inherent in certain prior art catheters through the inclusion of a soft, deformable member attached to the distal tip of the catheter. In one embodiment, the deformable tip member comprises an annular inflatable flexible, non-distensible "balloon" element attached to the distal end of the otherwise relatively rigid tip of the catheter. In this arrangement, the catheter itself is provided with a lumen extending substantially the entire length of the catheter and communicating with the deformable tip member whereby a fluid may be introduced to control the size, shape and firmness of the tip portion of the catheter. By selectively inflating the balloon tip, the effective area of the tip can be increased to reduce the overall force per unit area at the point of contact between the tip of the catheter and a blood vessel.

In a second embodiment, the soft deformable tip member comprises an annular plastic or rubber sleeve surrounding the otherwise rigid tip of the catheter and normally extending therebeyond by a predetermined distance. The thickness or composition of the sleeve is altered about a circumferential line so as to provide a preferred location for the folding and collapse of the sleeve as the terminal end of the sleeve is forced against body tissues. When the sleeve is made to collapse, the effective area of contact between the deformable tip and the body tissue increases to again reduce the pressure or force per unit area applied to the tissue.

OBJECTS

It is accordingly a principal object of the present invention to provide a new and improved catheter arrangement for medical applications.

Another object of the invention is to provide a catheter with a soft, deformable tip to thereby reduce the likelihood of damage to vascular tissue as the catheter is introduced and routed through the vascular system.

A still further object of the invention is to provide a catheter with an inflatable tip member whereby the shape and firmness of the distal end of the catheter can be controlled through the introduction of a fluid at the proximal end of the catheter.

Yet another object of the invention is to provide a catheter with a soft, deformable tip in the form of a sleeve member of a predetermined wall thickness profile such that the deformable tip member will collapse in a predictable manner to effectively increase the overall area of contact between the distal tip and body tissue which it contacts.

These and other objects and advantages of the invention will become apparent to those skilled in the art from the following detailed description of the preferred embodiments, especially when considered in conjunction with the accompanying drawings in which like numerals in the several views referred to corresponding parts.

DESCRIPTION OF THE DRAWINGS

FIG. 1 shows the distal tip portion of a conventional, prior art angiographic or diagnostic catheter;

FIG. 2 is a cross sectional view of a catheter having an inflatable tip secured thereto;

FIG. 3 is a cross sectional view of a catheter having an inflatable, non-distensible tip and an elastomeric band or sleeve in fluid communication therewith;

FIG. 4 is a cross sectional view of an angiographic catheter having a collapsable sleeve as its distal tip, the sleeve being illustrated in its uncompressed state;

FIG. 5 is a partial cross sectional view of FIG. 4 illustrating the sleeve in its collapsed state; and FIG. 6 is a partial cross sectional view of an alternative arrangement of a deformable tip on a catheter.

DESCRIPTION OF THE PREFERRED EMBODIMENTS

Referring first to FIG. 1, there is illustrated a longitudinal cross section of the distal end portion of a typical, prior art angiographic catheter. It is seen as comprising a predetermined length of flexible plastic tubing 10 having a central lumen 11 extending the length of the catheter thereof from its proximal end (not shown) to its distal end 12. The lumen 11 is provided so that angiographic dyes or other medicaments may be introduced into the catheter at its promixal end located outside the body and made to flow through the lumen to a predetermined site within the body at which the distal end 12 of the catheter is positioned.

It is to be especially noted that the distal tip 12 of the prior art catheter of FIG. 1 terminates in an abrupt edge 13 which is relatively sharp and, depending upon the type of material used for the body of the catheter 10 may possess sufficient rigidity to cause damage to vascular tissue, especially the endotheliel layer (tunica intima) lining the blood vessels as the catheter is routed through the vascular system.

To obviate this problem, in accordance with a first embodiment of the invention illustrated in FIG. 2, the catheter body 10 is provided with a double lumen, namely the lumen 11 for allowing the flow of angiographic dyes or other fluids and a further lumen 14 which also runs the entire length of the catheter. Secured to the distal tip of the catheter body is a flexible, non-distensible inflatable "balloon" member 15 which, in its expanded form, has the general shape of a toroid. The lumen 14 is arranged to communicate with the interior of the torus comprising the tip 15 while the lumen 11 communicates with the central opening 17 of that toroid. While fluid introduced into the lumen 11 at the proximal end of the catheter may ultimately be made to flow outwardly through the opening 17 of the soft, flexible tip 15, fluid introduced into the lumen 14 flows into the annular chamber 16 causing the tip member to become inflated. The tip member 15 is preferably formed from a bioaxially oriented or cross-linked polyolefin film and may have a thickness in the range of from 0.001 to 0.0025 inches. As such, when unflated or evacuated, it lacks rigidity and wraps about and conforms approximately to the shape of the end portion of the catheter body 10. However, once properly pressurized, it expands so as to increase the desired effective area of contact between the end of the catheter and and body tissue which it may abut as it is being routed or positioned within the body. The degree of inflation, of course, determines the degree of softness or deformability of the tip. Thus, the physician has considerable control over the tip properties of the catheter so that tissue damage will be minimized.

The toroidal balloon member 15 is preferably molded separate and apart from the catheter body 10 and then affixed thereto by thermal or chemical bonding but may be a cavity formed in the walls of the distal end of the catheter which, when filled with a fluid under pressure, causes the wall of the catheter itself to bulge.

FIG. 3 illustrates an alternative form of the embodiment of FIG. 2 which has been modified to incorporate a distensible elastomeric sleeve 18 for controlling the internal pressure of the non-extensible tip member 15. The distensible elastomeric sleeve 18 may be positioned at any point along the length of the catheter body 10 and, in fact, may be disposed at the extreme proximal end of the catheter at a location which remain outside of the body following its insertion in routing. The elastomeric sleeve is preferably disposed within a ring-like recess formed in the outside surface of the catheter body 10 and is suitably bonded in a fluid-tight fashion to the catheter body at its end edges thereof as indicated by numerals 19 and 20, respectively. A radial bore 21 extends from the recess surface of the catheter body to the secondary lumen 14. The radial bore 21, as well as the portion of the lumen 14 distally thereof, and the chamber 16 of the deformable tip 15 are filled with an incompressible fluid, and a suitable plug 22 is disposed within the lumen 14 at a point proximal of the radial bore 21.

When a force is applied to the tip member 15 in FIG. 3, the internal pressure of this tip member is increased causing bulging (inflation) of the elastomeric sleeve member 18 and a corresponding deflation of the tip member 15. The degree of deflation is, of course, proportional to the force exerted on it which, in turn, is a function of the "stiffness" of the elastomeric sleeve 18. A decrease in the volume in the tip member results in an increase in the area of contact between it and any mating surface against which it is forced.

When the sleeve 18 is located at a point external to the body, it may be suitably coupled to a transducer which will directly indicate the fluid pressure within the system causing it to expand.

With continued attention being directed to the tip member 15 in FIG. 3, it has been found expedient to incorporate a heavier toroidal ring as at 23 to define the annular opening 17. This ring has an outside diameter which is no greater than the internal diameter of any introducer through which the catheter must be passed during implantation. Using this construction, the tip member 15 will conform to a lumen smaller than the fully extended diameter of the tip member 15 because, as the force bearing on the wall increases, the internal pressure in the tip member will decrease due to the expansion of the elastomeric sleeve 18.

In practice, the lumen 14 may have a diameter in the range of from 0.002 inches to 0.004 inches extending from the tip member 15 through and including the radial side port 21. The lumen 14 may be continued to the proximal end of the catheter where the elastomeric sleeve 18 and its included side port 21 may be disposed.

As with the embodiment of FIG. 2, the tip member 15 is preferably formed from a non-extensible polyolefin film and may have a thickness range from 0.001 inch to 0.0025 inch. These dimensions and materials are set forth herein for illustrative purposes only and should not be considered as necessarily limiting the scope of the invention.

Referring next to FIG. 4, there is shown an alternative preferred embodiment of a catheter having a soft, deformable distal tip member affixed thereto. As viewed in FIG. 4, this tip member comprises a tubular sleeve 24 which surrounds and fits by means of a lap joint at the distal end of the catheter body 10 and the sleeve 24 extends beyond the distal end thereof by a predetermined length. Rather than being of a constant thickness, the walls of the flexible plastic sleeve 24 are shaped so that when the extreme tip or end 25 thereof is pushed against a stationary object with a predetermined low force, the tip will collapse to yield the configuration shown in FIG. 5. More specifically, the wall thickness of the portion of the tip member 24 extending beyond the end of the catheter 10 is generally constant but at the location identified by numeral 27 is relieved about an annular line, i.e., made to be of a lesser thickness, so as to fold about that circumferential line as a hinge. Likewise, the soft, compressible tip member 24 folds along the outside periphery of the end of the catheter as at 28 like a hinge. Instead of reducing the sleeve wall thickness to create a preferential hinge or fold line, it is also possible to achieve the desired folding pattern by having a discontinuity in the sleeve material so as to have a different (lower) stiffness than the adjacent material.

By properly choosing the durometer of the plastic material comprising the soft collapsible tip 24, it will posses a "memory" property so that when the tip is no longer compressed against a stationary object, it will again snap back to the shape illustrated in FIG. 4. It has also been found expedient to increase the amount of material surrounding the central opening 29 in the tip as at 30. This increase in material defines a ring which stablizes and strengthens the opening preventing it from sagging.

With reference to FIG. 5, it can be seen that when the tip member collapses, the effective area of contact between it and the object against which it is pressed is increased to thereby decrease the effective pressure exerted by the catheter structure against that tissue.

With no limitation intended and for illustrative purposes only, the lumen of the catheter may have a diameter of 0.045 inches and a wall thickness of 0.0085 inches at its distal end. The soft tip member 24 in FIGS. 4 and 5 is preferably about 0.005 inches thick but reducing to about 0.004 inches thick about the circular hinge line 27. When in its undeformed state, the distal end may exhibit a cross-sectional area of about 0.0012 square inches and, when collapsed as in FIG. 5, an area of 0.0041 square inches, representing a 3.41 times increase in area.

FIG. 6 illustrates a still further embodiment in which the catheter is fitted at its distal end with a tubular cylindrical tip member 31 fabricated from silastic or some other soft, deformable plastic material. When forces against an obstacle, the soft plastic tip will deform by spreading and bending to present an increased area of contact with respect to this obstacle.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and at various modifications, both as to equipment details and operating procedures can be effected without departing from the scope of the invention itself.

What is claimed is:

1. A catheter comprising:
  (a) an elongated flexible tubular member having at least one lumen extending the length thereof; and
  (b) a soft annular, deformable tip member affixed to the distal end of said catheter, said tip member including a circumferential preferential fold line located sufficiently close to the distal end of said tip member to allow collapse of said tip member along said preferential fold line upon being pressed against a relatively stationary surface without occluding said lumen.

2. The catheter as in claim wherein said tip member comprises:
  (a) a flexible, non-distensible, hollow fluid impervious container, the interior of said container being in fluid communication with a lumen in said tubular member.

3. The catheter as in claim 2 wherein said container is toroidal in shape.

4. The catheter as in claim 3 and further including a flexible plastic toroidal reinforcing ring disposed within the annular opening of said toroidal container.

5. The catheter as in claim 1 wherein said deformable tip member surrounds the distal end of said catheter.

6. The catheter as in claim 2 wherein said tip member is formed from a non-extensible polyolefin plastic film material.

7. The catheter as in claim 2 and further including:
  (a) a distensible segment sealingly affixed about its perimeter to said flexible tubular member at a location proximal of said tip member; and
  (b) a radial side port formed through the wall of said tubular member beneath said distensible segment, said side port communicating with said lumen.

8. The catheter as in claim 7 wherein said distensible segment comprises:
  (a) an elastomeric band surrounding said tubular member and covering said side port.

9. The catheter as in claim 1 wherein said deformable tip member comprises:
  (a) a flexible tubular sleeve member affixed to the distal end portion of said catheter and extending therebeyond for a predetermined distance, said flexible sleeve member having an annular zone defining said preferential fold line and located in the portion thereof extending beyond said distal end of said catheter.

10. The catheter as in claim 9 wherein said deformable tip member has an opening in said end of said tip member.

11. The catheter as in claim 8 wherein said opening is defined by an integrally formed reinforcing ring.

12. The catheter as in claim 9 wherein said tip member is formed from polyurethane.

13. The catheter as in claim 9 wherein the outer diameter of said sleeve member is the same as that of said elongated flexible tubular member.

* * * * *

UNITED STATES PATENT AND TRADEMARK OFFICE
CERTIFICATE OF CORRECTION

PATENT NO. : 4,531,943

DATED : July 30, 1985

INVENTOR(S) : Robert A. Van Tassel, Mark A. Rydell, Gilmore T. Schjeldahl

It is certified that error appears in the above-identified patent and that said Letters Patent is hereby corrected as shown below:

Column 3, line 34, delete "and" (second occurence) and put instead -- any --.

Column 6, line 3, after "claim" insert -- 1 --.

Signed and Sealed this

Nineteenth Day of July, 1988

Attest:

DONALD J. QUIGG

Attesting Officer

Commissioner of Patents and Trademarks